(12) United States Patent
Chan

(10) Patent No.: US 7,643,873 B2
(45) Date of Patent: Jan. 5, 2010

(54) EXERCISE DATA APPARATUS

(75) Inventor: Raymond Chan, Hong Kong (HK)

(73) Assignee: IDT Technology Limited, Hong Kong SAR (HK)

( * ) Notice: Subject to any disclaimer, the term of this patent is extended or adjusted under 35 U.S.C. 154(b) by 537 days.

(21) Appl. No.: 11/413,110

(22) Filed: Apr. 28, 2006

(65) Prior Publication Data

US 2007/0276271 A1    Nov. 29, 2007

(51) Int. Cl.
*A61B 5/0452*    (2006.01)
*A61B 5/0402*    (2006.01)
*A61B 5/5083*    (2006.01)

(52) U.S. Cl. .................. 600/520; 600/502; 600/529

(58) Field of Classification Search .............. 600/520, 600/502, 529
See application file for complete search history.

(56) References Cited

U.S. PATENT DOCUMENTS

| 4,367,752 A | * | 1/1983 | Jimenez et al. | 600/502 |
| 5,749,366 A | * | 5/1998 | Odagiri et al. | 600/502 |
| 6,030,342 A | * | 2/2000 | Amano et al. | 600/301 |

* cited by examiner

*Primary Examiner*—Carl H Layno
*Assistant Examiner*—Natashan N Patel
(74) *Attorney, Agent, or Firm*—Leydig, Voit & Mayer, Ltd.

(57) ABSTRACT

Exercise data apparatus for use on the body of a user during exercise, includes an electrocardiogram detector for detecting electrocardiogram data of the user during exercise; an attachment device for attaching the electrocardiogram detector onto the chest of the user; a motion detector for detecting body motion data indicative of steps of the user during exercise; a processor for calculating exercise data based on the electrocardiogram data detected by the electrocardiogram detector and the body motion data detected by the motion detector, the exercise data including at least one of heart rate, speed and distance, and calorie consumption of the user; and an output device for informing the user of the exercise data calculated.

25 Claims, 6 Drawing Sheets

EXERCISE DATA APPARATUS

The present invention relates to exercise data apparatus for measuring the heart rate and/or speed, etc. of a user during exercise.

BACKGROUND OF INVENTION

People who are engaged in exercise, especially jogging or running, usually want to keep track of their speed and distance covered as well as their heart rate information.

For speed/distance information, it is possible to use a GPS based sensor but its performance amongst buildings or in a forest is often hampered. Another option is using an acceleration sensor, but it normally needs calibration by the user running several hundred meters before play and this is thought inconvenient by many users, and in fact many acceleration-based sensors are unable to detect walking speed. In this regard, the use of a pedometer remains a low cost yet reasonably accurate solution, especially for amateurs.

Heart rate monitors are utilized to measure heart rate information, especially the chest-mounted type that is becoming increasing popular. Such heart rate monitors are more delicate electronic devices than pedometers in general and are often used at different positions on the body of a person.

The invention seeks to provide new or otherwise improved exercise data apparatus that are relatively low cost and more convenient to use.

SUMMARY OF THE INVENTION

According to the invention, there is provided exercise data apparatus for use on the body of a user during exercise, comprising:
  an electrocardiogram detector for detecting electrocardiogram data of said user during exercise;
  attachment means for attaching the electrocardiogram detector onto the chest of said user;
  a motion detector for detecting body motion data indicative of steps of said user during exercise;
  a processor for calculating exercise data based on the electrocardiogram data detected by the electrocardiogram detector and the body motion data detected by the motion detector, the exercise data comprising at least one of heart rate, speed and distance and calorie consumption of said user; and
  an output device for informing said user of the calculated exercise data.

Preferably, the motion detector comprises a pedometer.

More preferably, the pedometer is physically associated with the electrocardiogram detector for attachment onto the chest of said user by the attachment means.

More preferably, the pedometer is one of a pendulum type sensor and a piezoelectric type sensor.

Preferably, the motion detector comprises an accelerometer.

More preferably, the accelerometer is wrist-mounted.

More preferably, the accelerometer is one of an integrated circuit type sensor and a piezoelectric type sensor.

In a first preferred embodiment, the exercise data apparatus comprise a sensor unit, a data unit separate from the sensor unit, and a signal link between the sensor unit and the data unit, wherein:
  the sensor unit comprises the electrocardiogram detector, the attachment means and the motion detector; and
  the data unit comprises the processor, the output device and individual attachment means for attachment onto a wrist of said user.

More preferably, the motion detector comprises a pedometer.

More preferably, the output device comprises a display for displaying the calculated exercise data.

More preferably, the signal link comprises:
  a wireless transmitter at the sensor unit for transmitting a wireless signal indicative of the electrocardiogram data detected by the electrocardiogram detector and the body motion data detected by the motion detector; and
  a wireless receiver at the data unit for receiving the wireless signal, based on which the processor is to calculate the exercise data.

In a second preferred embodiment, the exercise data apparatus comprise a sensor unit, a data unit separate from the sensor unit, and a signal link between the sensor unit and the data unit, wherein:
  the sensor unit comprises the electrocardiogram detector and the attachment means; and
  the data unit comprises the processor, the motion detector, the output device and individual attachment means for attachment onto a wrist of said user.

More preferably, the motion detector comprises an accelerometer.

More preferably, the output device comprises a display for displaying the calculated exercise data.

More preferably, the signal link comprises:
  a wireless transmitter at the sensor unit for transmitting a wireless signal indicative of the electrocardiogram data detected by the electrocardiogram detector; and
  a wireless receiver at the data unit for receiving the wireless signal, based on which and the body motion data detected by the motion detector the processor is to calculate the exercise data.

In a third preferred embodiment, the exercise data apparatus comprise a sensor unit, a data unit separate from the sensor unit, and a signal link between the sensor unit and the data unit, wherein:
  the sensor unit comprises the electrocardiogram detector, the attachment means, the processor and the motion detector; and
  the data unit comprises the output device and individual attachment means for attachment onto an ear of said user.

More preferably, the motion detector comprises a pedometer.

More preferably, the output device comprises an audio device for announcing the calculated exercise data.

More preferably, the signal link comprises a wired connection for transmitting the exercise data calculated by the processor to the output device.

It is preferred that the exercise data apparatus include input means for input of body height and sex of said user, wherein the processor is programmed to calculate speed and distance based on steps detected by the pedometer and variable stride calculated based on body height and sex inputted and pace frequency detected by the motion detector.

It is further preferred that the input means also enables input of fitness level of said user, and the processor is programmed to calculate calorie consumption based on speed calculated, heart rate detected by the electrocardiogram detector and fitness level inputted.

Advantageously, the attachment means comprises a belt.

It is preferred that the processor is programmed to determine a variable stride of said user for calculation of the distance, the variable stride being determined based on gender, body height and pace frequency of said user.

It is further preferred that the variable stride is determined according to the formula:

$$\text{Stride} = a*(F-b)^2 + c*H*G$$

wherein:
F is pace frequency
G is gender coefficient: 0.7 for female/0.8 for male
H is body height
a, b and c are parameters whose values are dependent upon that of F as follows:

| | |
|---|---|
| $[a, b, c] = [0, 0, 0.5]$ | $(F < 1.5 \text{ Hz})$ |
| $[a, b, c] = [0.3, 1.5, 0.5]$ | $(1.5 \text{ Hz} <= F < 2.0 \text{ Hz})$ |
| $[a, b, c] = [0.8, 1.9, 0.55]$ | $(2.0 \text{ Hz} <= F < 2.5 \text{ Hz})$ |
| $[a, b, c] = [-0.5, 2.9, 1.15]$ | $(2.5 \text{ Hz} <= F < 3.3 \text{ Hz})$ |
| $[a, b, c] = [0, 0, 0.97]$ | $(F >= 3.3 \text{ Hz})$ |

It is preferred that the processor is programmed to calculate the calorie consumption based on the weight, fitness level and heart rate of said user.

It is further preferred that the calorie consumption is calculated according to the formula:

$$\frac{\text{Calorie}}{\text{consumption}} = TI * \text{Weight} * (\text{instant } HR / \text{maximum } HR) - AF$$

wherein HR is the heart rate, and TI and AF are Training Index and Activity Factor respectively dependent upon $VO_2$ percentage (% $VO_2$ max) that being instant $VO_2$ divided by $VO_2$ max, wherein instant $Vo_2$ is dependent upon the speed.

It is yet further preferred that the instant $Vo_2$ is determined according to one of the following formulae:

Walking: $VO_2 = 0.1 * \text{speed} + 3.5$

Running: $VO_2 = 0.2 * \text{speed} + 3.5$

BRIEF DESCRIPTION OF DRAWINGS

The invention will now be more particularly described, by way of example only, with reference to the accompanying drawings, in which.

DETAILED DESCRIPTION OF PREFERRED EMBODIMENTS

Figure 1:
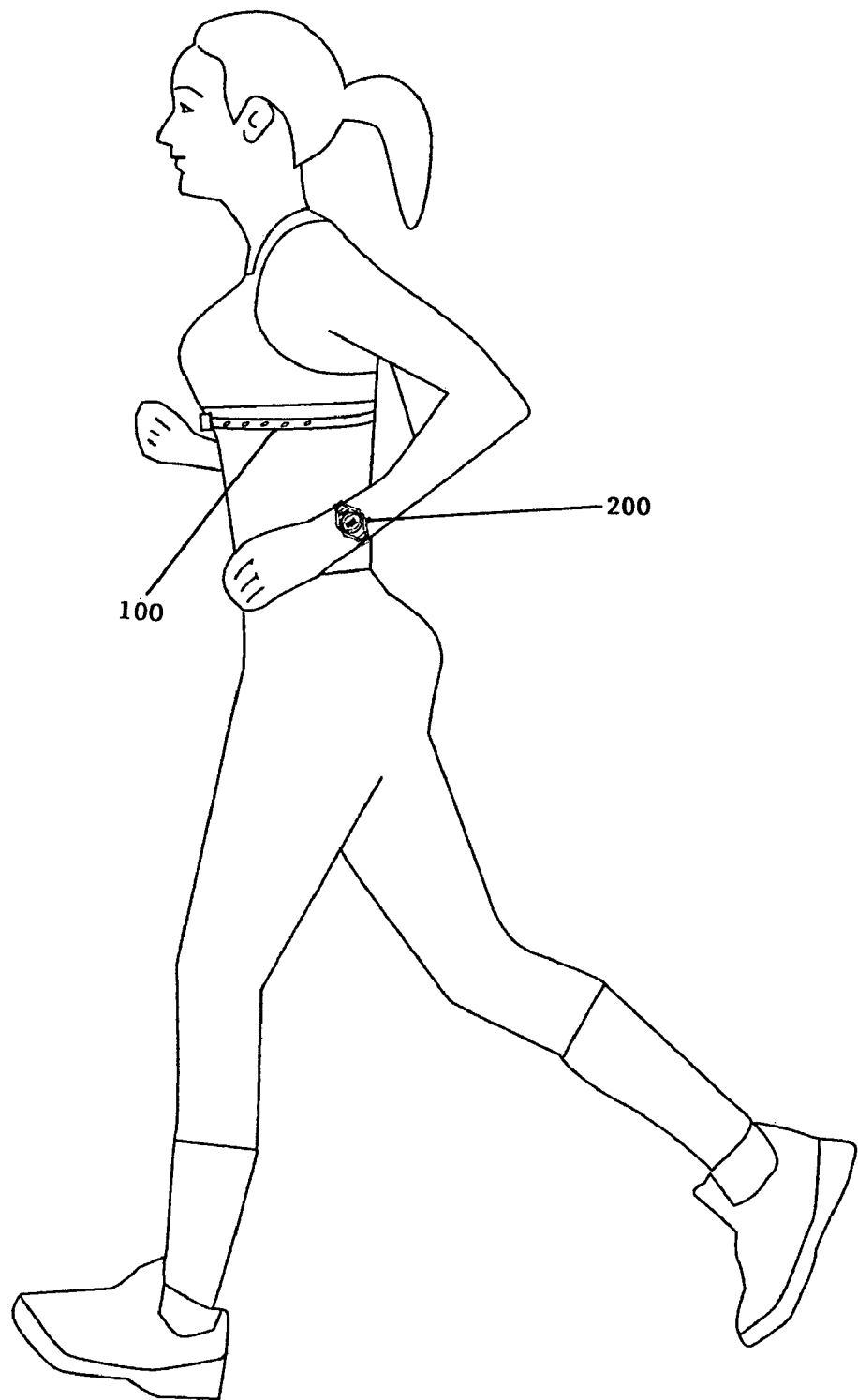
FIG. 1 is a schematic diagram showing a female user using a first embodiment of exercise data apparatus in accordance with the invention, comprising a sensor unit on her chest and a data unit on her wrist.
Figure 2:
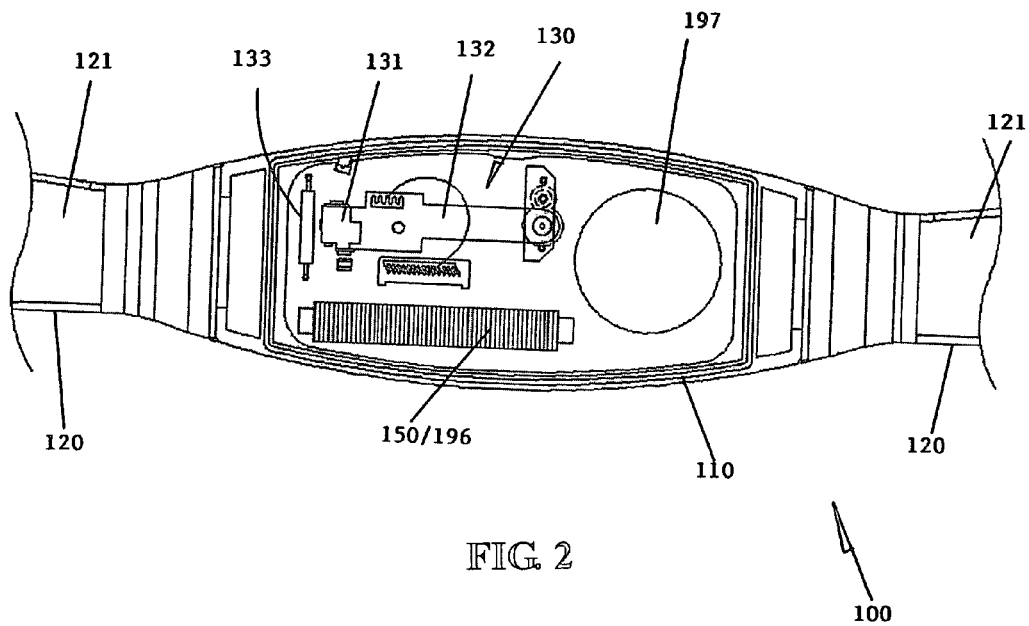
FIG. 2 is a fragmentary front view of the sensor unit of FIG. 1, showing some of its internal components.
Figure 3:
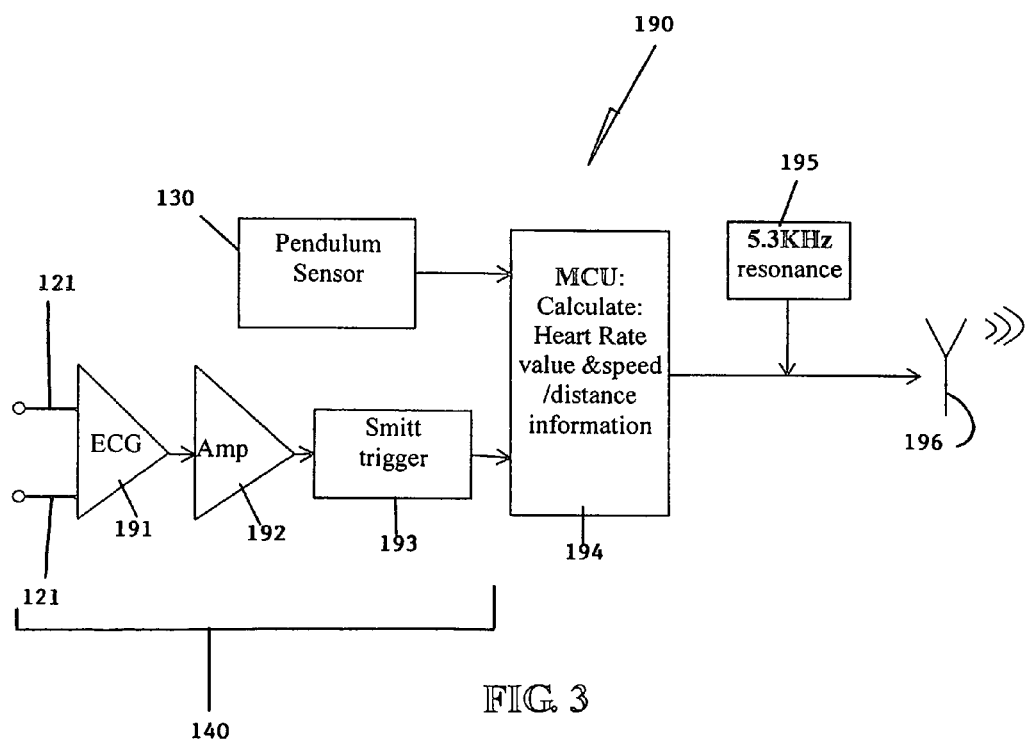
FIG. 3 is a functional block diagram of the operating circuit of the sensor unit of FIG. 2.
Figure 4:
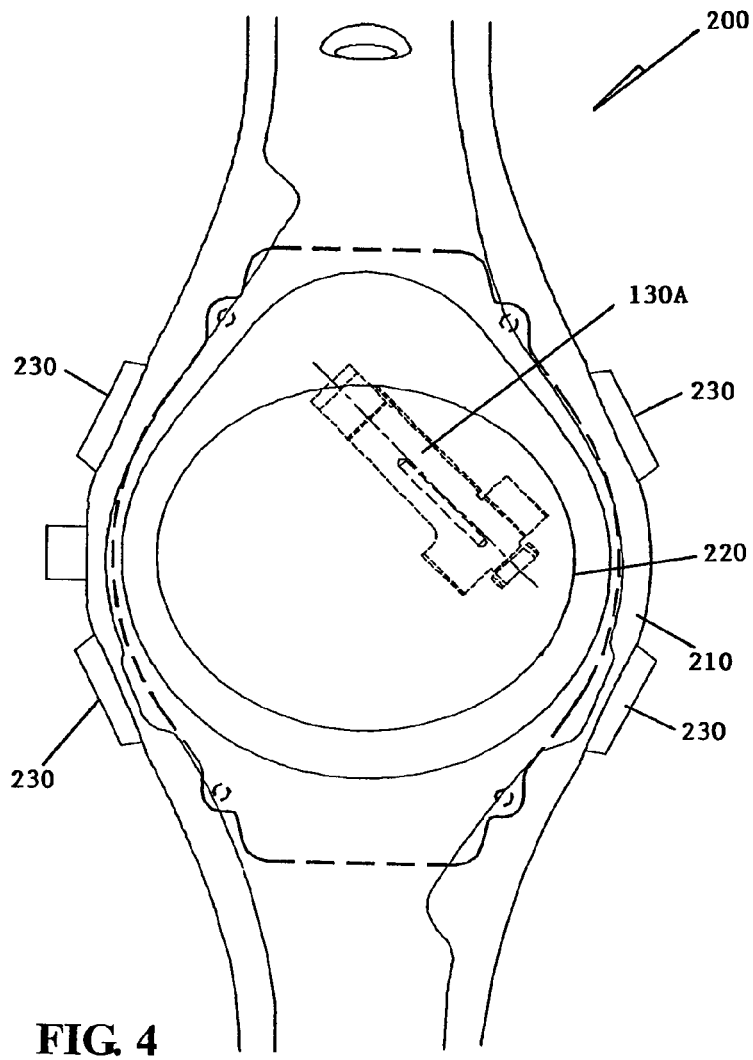
FIG. 4 is a fragmentary front view of the data unit of FIG. 1, showing some of its internal components.
Figure 5:
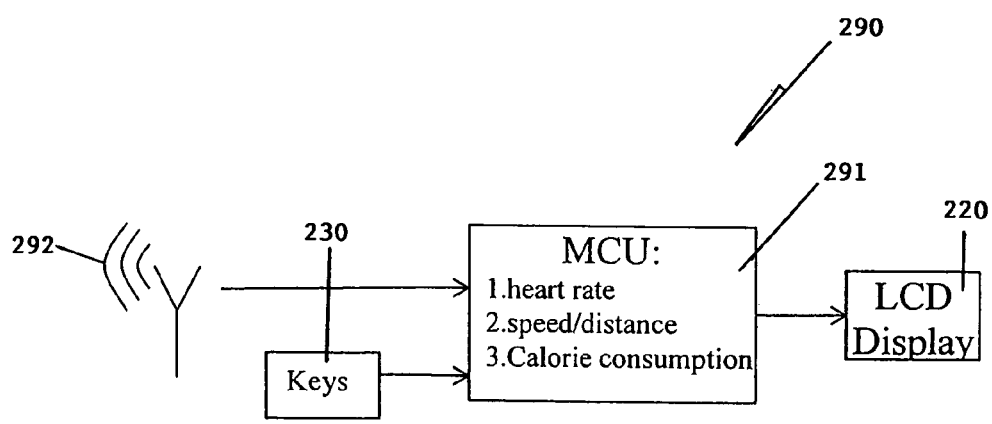
FIG. 5 is a functional block diagram of the operating circuit of the data unit of FIG. 4.

Referring initially to FIGS. 1 to 5 of the drawings, there are shown first exercise data apparatus embodying the invention, which comprise two separate units i.e. a sensor unit 100 and a data unit 200 that are in communication with each other via a wireless signal link for operation, such as an RF (radio frequency) signal link. Alternatively, a wired connection/link from the sensor unit 100 to the data unit 200 may be employed. The sensor unit 100 is in the form of a chest belt, having a casing 110 and a chest belt (or strap) 120 for attaching the overall unit 100 horizontally onto the chest of a user, i.e. a female user as depicted. Housed in the casing 110 are a pedometer 130 for detecting body motion data indicative of steps of the user during exercise, an electrocardiogram (ECG) detection circuit or detector 140 for detecting ECG data of the user during exercise, and an RF transmitter 150 for transmitting a wireless RF signal carrying or indicative of both such data. Such modules 130, 140 and 150 are physically associated together and are powered by a common DC power source in the casing 110, which is conveniently provided by a battery pack or cells that may be replaced or recharged.

The sensor unit 100 has an electronic operating circuit 190 located in the casing 110, which is powered by a battery 197 and includes an ECG sensor 191 comprising a pair of electrodes 121 on the rear side at opposite ends of the belt 120 for bearing against the user's chest to detect her heartbeat. As part of the operating circuit 190, connected in series from the output of the ECG electrodes 121 are an amplifier 192, a Smitt trigger 193, an MCU (microprocessor control unit) 194, an RF modulator 195 at 5.3 kHz resonance and an antenna 196. The modulator 195 and antenna 196 are key components of the transmitter 150.

The ECG sensor 191/electrodes 121, amplifier 192 and Smitt trigger 193 together constitute the ECG detector 140. The detected heartbeat is an ECG signal, which will be amplified by the amplifier 192 and then converted by the Smitt trigger 193 into a pulse train for subsequent processing by the MCU 194. Compared with general triggers, the Smitt trigger 193 offers the advantage of better control over false trigger signals as may be caused by noises.

The pedometer 130 is of a pendulum type sensor, formed by a permanent magnet 131 supported at the free end of a proximal resiliently pivotable cantilever 132 proximal to a vertical reed switch 133. As the user moves her body up and down during walking, jogging or running exercise, the magnet 131 is swung in opposite directions past the reed switch 133, which thus opens and closes to detect and indicate the steps or paces (body motion) of the user. The reed switch 133 is connected to an input of the MCU 194, separate from that for the Smitt trigger 193.

As an alternative, a pedometer of a piezoelectric type sensor may be employed instead, which is more compact in size and is often more durable and reliable.

The MCU 194 is programmed to, inter alia, calculate the heart rate (in beats per minute) based on the heartbeat pulses detected by the ECG electrodes 121 as regulated by the Smitt trigger 193 and then to transform the calculated heart rate into a coded data packet. The MCU 194 will also count the user's steps detected by the pedometer 130 against time and then determine the pace frequency and a variable stride (defined below) to calculate the distance covered by and the speed of the user.

Besides the various aforesaid calculated data, the MCU 194 will insert a device ID code that identifies the data unit 200 as well as check bits for error correction, together being encoded as a coded data packet. The coded data packet is outputted to the transmitter 150 for transmission as a wireless RF signal at 5.3 kHz resonance under the control of the MCU 194, for reception by the data unit 200.

The data unit 200 is in the form of a wristwatch which has a watch case 210 fitted with straps for attaching the overall device onto a wrist of the user. The data unit 200 includes an LCD display 220 for outputting various data including exercise data, and a number of keys 230 for operation control and data input including inputting the user's personal data such as body height, sex and fitness level. Such data may alternatively be inputted using a PC or PDA via wired or wireless communication.

Housed in the watch case 210 is an electronic operating circuit 290 which is built based on an MCU 291 and includes an RF receiver 292 connected thereto for receiving the RF signal, i.e. coded data packet, from the sensor unit 100. The display 220 and keys 230 are also are connected the MCU 291 for operation.

The MCU 291 is programmed to, inter alia, demodulate and process the coded data packet to extract the encoded data therefrom i.e. the heart rate, speed and distance, and then display the same on the LCD display 220. The MCU 291 will also perform calculation to determine certain other exercise data, and in particular calorie consumption or burned by the user in the exercise, and display the result. The pace frequency and elapsed time may also be displayed.

The operating circuit 290 with MCU 291 also provides the standard time/date keeping watch functions including stopwatch and alarm functions.

For the detection of heart rate (HR), an ECG based chest belt 100 is preferred because it is effective for users either at rest or during light or heavy exercise.

The maximum heart rate that people of different ages can achieve in general can be determined using the simple formula:

Maximum Heart Rate=220−Age

The instant HR represented as a percentage of the maximum heart rate (i.e. % HR) gives a reasonable indication of the intensity of exercise:

% HR=instant HR/maximum HR

With regard to speed and distance, speed is calculated by dividing distance by time:

Speed=Distance/Time

Distance is determined by paces or steps multiplied by stride:

Distance=Steps×Stride

In this formula, the steps are counted using the pedometer 130 that is built into the chest belt 100. The sensitivity of the pedometer 130 is calibrated to an optimal level so that counting of steps for both walking and running/jogging types of body motion can be optimized.

Traditionally, a fixed value for the stride is chosen and entered for a specific person primarily according to his/her body height. This is often unsatisfactory for accuracy.

The stride used in the above formula for distance is a variable stride (ST) that is calculated for each step dependent upon the sex/gender and body height of the person as entered using the keys 230 and the prevailing pace frequency:

Stride=f(Pace Frequency, Gender, Body Height)

The pace frequency is determined by the MCU 194 for every step, instantaneously in practice, and preferably averaged over a certain immediately preceding period of time or number of steps.

The detailed stride formula is:

$ST = a*(F−b)^2 + c*H*G$ in which a, b and c are parameters whose values are dependent upon that of F as follows:

| | |
|---|---|
| $[a, b, c] = [0, 0, 0.5]$ | $(F < 1.5 \text{ Hz})$ |
| $[a, b, c] = [0.3, 1.5, 0.5]$ | $(1.5 \text{ Hz} <= F < 2.0 \text{ Hz})$ |
| $[a, b, c] = [0.8, 1.9, 0.55]$ | $(2.0 \text{ Hz} <= F < 2.5 \text{ Hz})$ |
| $[a, b, c] = [−0.5, 2.9, 1.15]$ | $(2.5 \text{ Hz} <= F < 3.3 \text{ Hz})$ |
| $[a, b, c] = [0, 0, 0.97]$ | $(F >= 3.3 \text{ Hz})$ | where:

F is pace frequency in steps per second

G is gender coefficient: 0.7 for female/0.8 for male

H is height in meters

Figure 6:
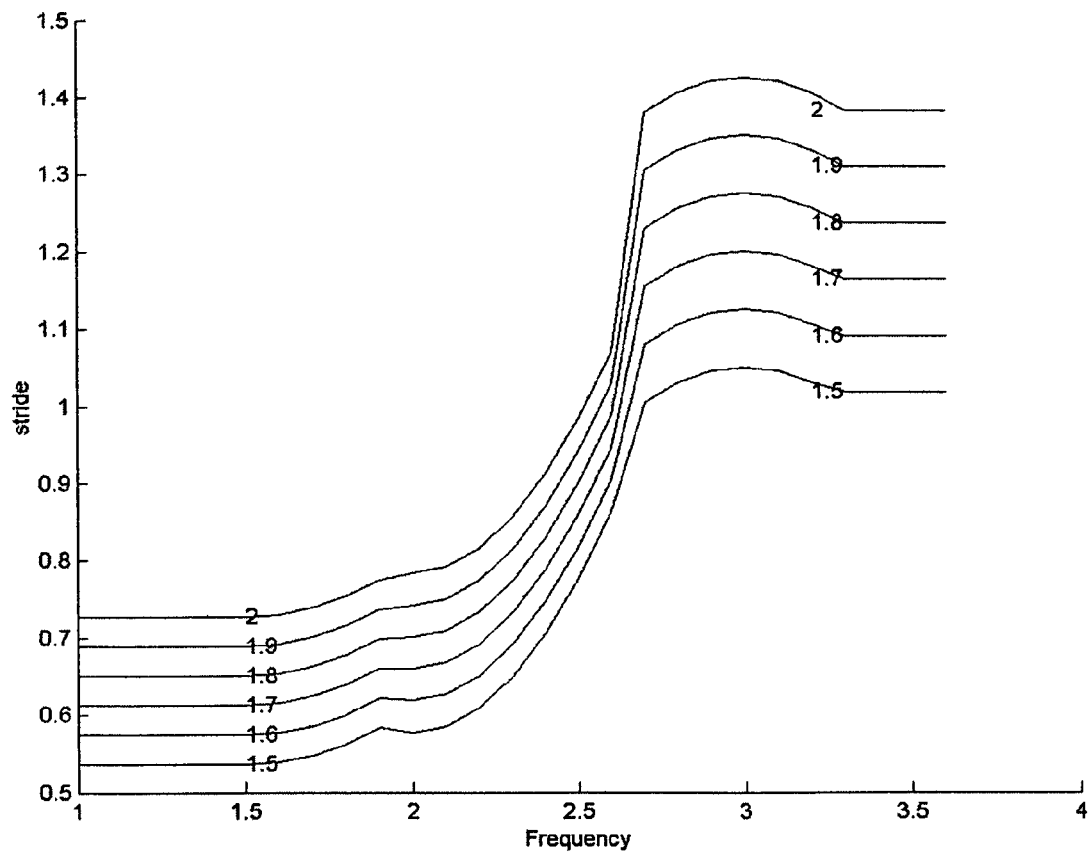
FIG. 6 is a graph showing typical stride curves as a function of pace frequency for female users of different body heights.

The stride formula is derived from volume statistical testing and analysis. A graph showing instant stride curves as a function of the pace frequency for female users of different body heights is depicted in FIG. 6.

The processor 291 is programmed to calculate the speed and distance based on the steps detected by the pedometer 130 and the variable stride determined as described above based on the body height and sex inputted by the user and the pace frequency detected by the pedometer 130.

The processor 291 is also programmed to calculate the calorie consumption during exercise based on the speed calculated as described above, the heart rate detected by the ECG detector 140 and the fitness level inputted by the user.

The calorie consumption is calculated from the heart rate (HR) and speed, etc. according to the following equation:

Calorie consumption per hr=$TI$*Weight* % $HR$−$AF$

Training Index (TI) and Activity Factor (AF) are standard parameters for exercise, and they are dependent upon $VO_2$ percentage (% $VO_2$ max) as follows:

| % $VO_2$ max | TI | AF |
|---|---|---|
| 50%-60% | 6 | 400 |
| 60%-70% | 8 | 580 |
| 70%-80% | 12 | 1000 |
| 80%-90% | 18 | 1720 |
| 90%-100% | 22 | 2260 |

$VO_2$ percentage (% $VO_2$ max) is the ratio of instant $VO_2$ divided by $VO_2$ max:

% $VO_2$ max=$VO_2$/$VO_2$ max $VO_2$ max is defined as the maximum rate of oxygen consumption, often expressed in liters per minute (L/min) or millimeters per kg body weight per minute (ml/kg/min). Because oxygen consumption is linearly related to energy expenditure, $VO_2$ max is a measure of capacity of a person to generate the energy required for endurance activities. It is one of the most important factors determining the ability to exer cise for longer than four to five minutes, or one's own fitness level. $VO_2$ max can be calculated as follows:

Male: $VO_2$ max=67.195+6.7235(ACT-S)−0.381(age)−0.754(BMI)

Female: $VO_2$ max=56.363+6.7235(ACT-S)−0.381(age)−0.754(BMI)

where ACT-S is activity score (0,1,2) inputted by user using the keys 230

BMI=weight (kg)/square of height (m)

Instant $Vo_2$ represents the intensity of a specific type of exercise, and is calculated as follows:

Walking: $VO_2$=0.1*speed+3.5

Running: $VO_2$=0.2*speed+3.5

(speed in miles per hour)

The pedometer 130 counts steps and is best placed on the user's trunk (e.g. chest) by reason of its simple up and down motion while the user is running or jogging. For more sophisticate detection, an accelerometer 130A may be used instead, as depicted in dotted line in FIG. 4, which is installed in the wrist-mounted data unit 200. The accelerometer 130A is an IC (integrated circuit) type or piezoelectric type acceleration sensor, the latter type being widely used sensors in the fields of vibration and shock instrumentation.

For the present purpose, the accelerometer 130A is used to detect the swinging motion—reversals in direction—of the relevant arm of the user during running or jogging exercise so as to give an indication of the user's steps i.e. to indirectly count her steps.

As the sensor unit 100 does no longer incorporate the motion detector 130A, its MCU 194 is not responsible for calculating the user's traveling speed and distance and its transmitter 150 will only transmit, primarily, the ECG data detected by the ECG detector 140 to the data unit 200. At the data unit 200, the MCU 291 instead will count the user's steps sensed by the accelerometer 130A against time and determine the pace frequency and the variable stride to calculate the distance covered by and the speed of the user. The MCU 291 will also calculate the user's calorie consumption based on the received ECG data and the step-related data determined in situ.

Figure 7:
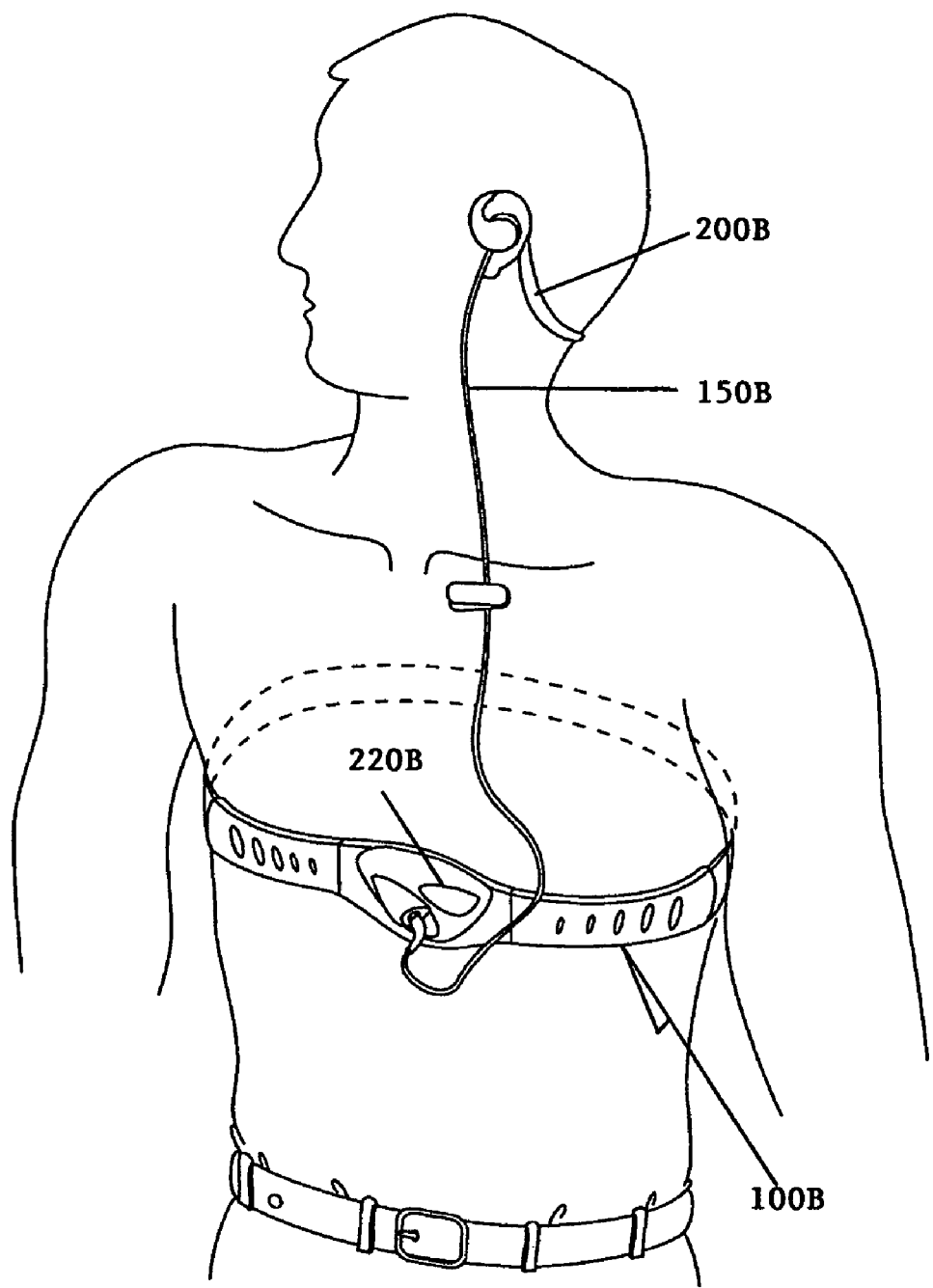
FIG. 7 is a schematic diagram showing a male user using a second embodiment of exercise data apparatus in accordance with the invention.
Figure 8:
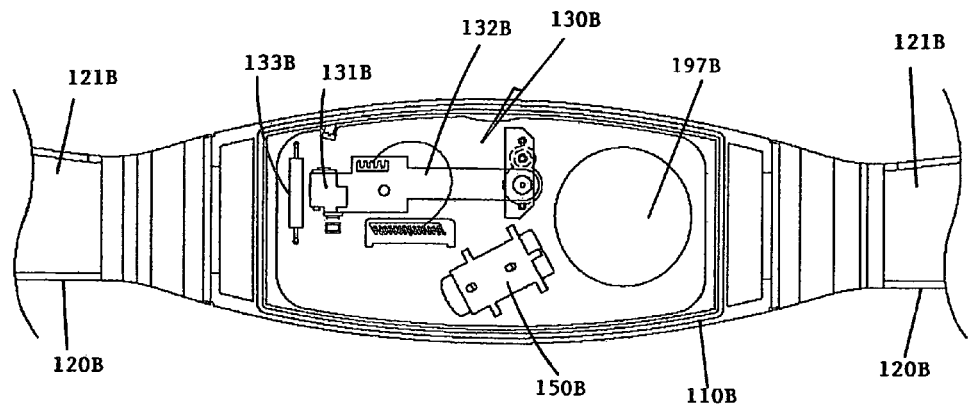
FIG. 8 is a fragmentary front view of the apparatus of FIG. 7, showing some of its internal components.
Figure 9:
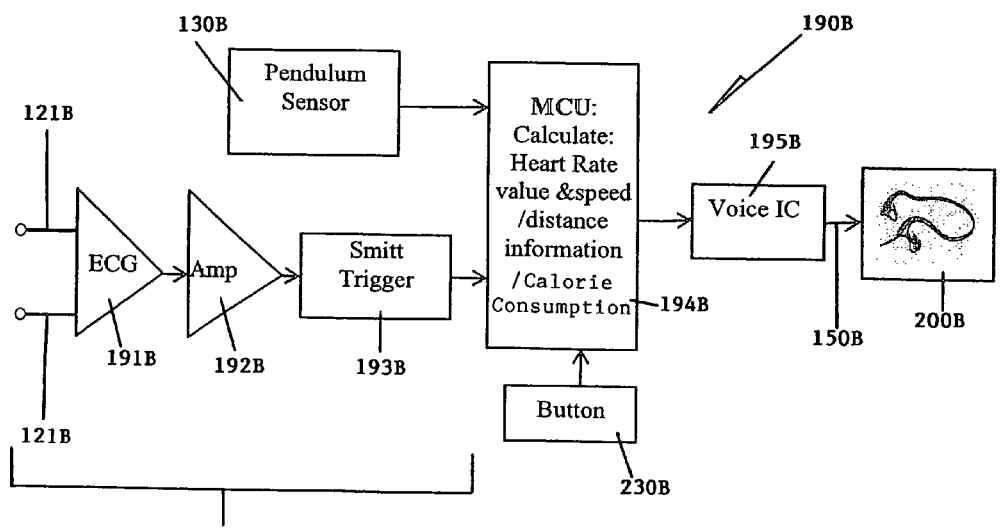
FIG. 9 is a functional block diagram of the operating circuit of the apparatus of FIG. 7.

FIGS. 7 to 9 show second exercise data apparatus embodying the invention used by a male user, which have a similar basic construction and operate in a similar manner as the first exercise data apparatus (with pedometer) described above, with equivalent parts designated by the same reference numerals suffixed by a letter "B". The major differences lie in the sensor unit 100B being constructed to perform all of the data sensing and processing functions and the data unit 200B being reduced to an audio device i.e. earphone 200B and connected to the sensor unit 100B by means of a wired connection/link 150B.

The chest belt 120B attaches the overall sensor unit 100B onto the user for ECG data detection using the on-belt electrodes 121B. Buttons 230B and LCD display 220B on the casing 110B of the sensor unit 100B enable manual input of the sex/gender, body height and fitness level of the user. The earphone 200B has individual attachment means for attachment onto the user's ears. As part of the operating circuit 190B in the sensor unit's casing 110B, the ECG detector 140B/121B detects the user's ECG data (i.e. heart beats) and the pedometer 130B counts his steps. Further, the MCU 194B is programmed to calculate the heart rate based on the heartbeat pulses detected by the ECG electrodes 121B as regulated by the amplifier 192B and Smitt trigger 193B, to count the user's steps detected by the pedometer 130B against time and determine the pace frequency and the variable stride (using the inputted sex and height), and then to calculate the user's traveling speed and distance. The MCU 194B may also calculate the calorie burned by the user based on the calculated speed, the detected heart rate and the inputted fitness level.

The operating circuit 190B includes a voice IC 195B connected at the output of the MCU 194B for converting the calculated exercise data, i.e. the heart rate, speed/distance and calorie consumption, into speech form and then transmitting the same along the wire 150B to the earphone 200B for announcing to the user. To enable connection of the earphone 200B by its plug, the sensor unit 100B includes a phone jack module 150BB.

The subject invention provides low-cost exercise data apparatus for measuring the heart rate, speed and distance of a person during walking, jogging or running exercise and for calculating his/her energy or calorie consumption from both the heart rate and the speed.

The invention has been given by way of example only, and various modifications of and/or alterations to the described embodiments may be made by persons skilled in the art without departing from the scope of the invention as specified in the appended claims.

The invention claimed is:

1. An exercise data apparatus for use on the body of a user during exercise, comprising:

an electrocardiogram detector for detecting electrocardiogram data of a user during exercise;

attachment means for attaching the electrocardiogram detector onto the chest of the user;

a motion detector for detecting body motion data indicative of steps of the user during exercise;

a processor for calculating exercise data based on the electrocardiogram data detected by the electrocardiogram detector and the body motion data detected by the motion detector, the exercise data comprising at least one of heart rate, speed and distance, and calorie consumption of the user, wherein the processor is programmed to calculate the calorie consumption based on weight, fitness level, and heart rate of the user; and an output device for informing the user of the exercise data calculated, wherein the calorie consumption is calculated according to the formula:

$$\text{Calorie consumption} = TI * \text{Weight} * (\text{instant } HR / \text{maximum } HR) - AF,$$

wherein
HR is the heart rate of the user,
TI and AF are Training Index and Activity Factor, respectively, and are related to $VO_2$ percentage,
$VO_2$ is oxygen consumption of the user, $VO_2$max is maximum rate of oxygen consumption by the user, and $VO_2$ percentage is the percentage of $VO_2$max being consumed by the user, and
when $VO_2$ percentage is 50% to 60%, TI=6 and AF=400,
when $VO_2$ percentage is 60% to 70%, TI=8 and AF=580,
when $VO_2$ percentage is 70% to 80%, TI=12 and AF=1,000, when VO$_2$ percentage is 80% to 90%, TI=18 and AF=1,720, and when VO$_2$ percentage is 90% to 100%, TI=22 and AF=2,260.

2. The exercise data apparatus as claimed in claim 1, wherein the motion detector comprises a pedometer.

3. The exercise data apparatus as claimed in claim 2, wherein the pedometer is physically associated with the electrocardiogram detector for attachment onto the chest of the user by the attachment means.

4. The exercise data apparatus as claimed in claim 2, wherein the pedometer is one of a pendulum sensor and a piezoelectric sensor.

5. The exercise data apparatus as claimed in claim 1, wherein the motion detector comprises an accelerometer.

6. The exercise data apparatus as claimed in claim 5, wherein the accelerometer is wrist-mounted.

7. The exercise data apparatus as claimed in claim 5, wherein the accelerometer is one of an integrated circuit sensor and a piezoelectric sensor.

8. The exercise data apparatus as claimed in claim 1, comprising a sensor unit, a data unit separate from the sensor unit, and a signal link between the sensor unit and the data unit, wherein:

the sensor unit comprises the electrocardiogram detector, the attachment means, and the motion detector; and the data unit comprises the processor, the output device, and individual attachment means for attachment onto a wrist of the user.

9. The exercise data apparatus as claimed in claim 8, wherein the motion detector comprises a pedometer.

10. The exercise data apparatus as claimed in claim 8, wherein the output device comprises a display for displaying the exercise data calculated.

11. The exercise data apparatus as claimed in claim 8, wherein the signal link comprises:

a wireless transmitter at the sensor unit for transmitting a wireless signal indicative of the electrocardiogram data detected by the electrocardiogram detector and the body motion data detected by the motion detector; and a wireless receiver at the data unit for receiving the wireless signal, based on which the processor calculates the exercise data.

12. The exercise data apparatus as claimed in claim 1, comprising a sensor unit, a data unit separate from the sensor unit, and a signal link between the sensor unit and the data unit, wherein:

the sensor unit comprises the electrocardiogram detector and the attachment means; and the data unit comprises the processor, the motion detector, the output device, and individual attachment means for attachment onto a wrist of the user.

13. The exercise data apparatus as claimed in claim 12, wherein the motion detector comprises an accelerometer.

14. The exercise data apparatus as claimed in claim 12, wherein the output device comprises a display for displaying the exercise data calculated.

15. The exercise data apparatus as claimed in claim 12, wherein the signal link comprises:

a wireless transmitter at the sensor unit for transmitting a wireless signal indicative of the electrocardiogram data detected by the electrocardiogram detector; and a wireless receiver at the data unit for receiving the wireless signal, based on which and on the body motion data detected by the motion detector, the processor calculates the exercise data.

16. The exercise data apparatus as claimed in claim 1, comprising a sensor unit, a data unit separate from the sensor unit, and a signal link between the sensor unit and the data unit, wherein:

the sensor unit comprises the electrocardiogram detector, the attachment means, the processor, and the motion detector; and the data unit comprises the output device and individual attachment means for attachment onto an ear of the user.

17. The exercise data apparatus as claimed in claim 16, wherein the motion detector comprises a pedometer.

18. The exercise data apparatus as claimed in claim 16, wherein the output device comprises an audio device for announcing the exercise data calculated.

19. The exercise data apparatus as claimed in claim 16, wherein the signal link comprises a wired connection for transmitting the exercise data calculated by the processor to the output device.

20. The exercise data apparatus as claimed in claim 1, wherein the attachment means comprises a belt.

21. The exercise data apparatus as claimed in claim 1, wherein instantaneous VO$_2$ is determined for Walking as VO$_2$=0.1*speed+3.5, and Running as VO$_2$=0.2*speed+3.5.

22. An exercise data apparatus for use on the body of a user during exercise comprising:

an electrocardiogram detector for detecting electrocardiogram data of a user during exercise;

attachment means for attaching the electrocardiogram detector onto the chest of the user;

a motion detector for detecting body motion data indicative of steps of the user during exercise;

a processor for calculating exercise data based on the electrocardiogram data detected by the electrocardiogram detector and the body motion data detected by the motion detector, the exercise data comprising at least one of heart rate, speed and distance, and calorie consumption of the user, wherein the processor is programmed to determine a variable stride of the user for calculation of the distance, the variable stride being determined based on gender, body height, and pace frequency of the user, and the variable stride is determined according to the formula Stride=$a*(F-b)^2+c*H*G$, wherein F is pace frequency in Hz, G is gender coefficient and is 0.7 for females and 0.8 for males, H is body height in meters, and a, b, and c are parameters that have respective values depending upon the pace frequency F and when F is less than 1.5 Hz, a=0, b=0, and c=0.5, when F is at least 1.5 Hz and less than 2.0 Hz, a–0.3, b=1.5, and c=0.5, when F is at least 0.2 Hz and less than 2.5 Hz, a=0.8, b=1.9, and c=0.55, when F is at least 2.5 Hz and less 3.3 Hz, a=−0.5, b=2.9, and c=1.15, and when F is at least 3.3 Hz, a=0, b=0, and c=0.97; and an output device for informing the user of the exercise data calculated.

23. The exercise data apparatus as claimed in claim 22, comprising a sensor unit, a data unit separate from the sensor unit, and a signal link between the sensor unit and the data unit, wherein:
- the sensor unit comprises the electrocardiogram detector, the attachment means, and the motion detector; and
- the data unit comprises the processor, the output device, and individual attachment means for attachment onto a wrist of the user.

24. The exercise data apparatus as claimed in claim 22, comprising a sensor unit, a data unit separate from the sensor unit, and a signal link between the sensor unit and the data unit, wherein:
- the sensor unit comprises the electrocardiogram detector and the attachment means; and
- the data unit comprises the processor, the motion detector, the output device, and individual attachment means for attachment onto a wrist of the user.

25. The exercise data apparatus as claimed in claim 22, comprising a sensor unit, a data unit separate from the sensor unit, and a signal link between the sensor unit and the data unit, wherein:
- the sensor unit comprises the electrocardiogram detector, the attachment means, the processor, and the motion detector; and
- the data unit comprises the output device and individual attachment means for attachment onto an ear of the user.

* * * * *